US009561296B1

United States Patent
Sobhy

(10) Patent No.: US 9,561,296 B1
(45) Date of Patent: Feb. 7, 2017

(54) DISINFECTING APPARATUS FOR RESTRAINING DEVICES

(71) Applicant: Shawki Sobhy, Oak Lawn, IL (US)

(72) Inventor: Shawki Sobhy, Oak Lawn, IL (US)

( * ) Notice: Subject to any disclaimer, the term of this patent is extended or adjusted under 35 U.S.C. 154(b) by 0 days.

(21) Appl. No.: 14/823,171

(22) Filed: Aug. 11, 2015

(51) Int. Cl.
*A61L 2/18* (2006.01)
*A61L 2/24* (2006.01)

(52) U.S. Cl.
CPC ... *A61L 2/18* (2013.01); *A61L 2/24* (2013.01)

(58) Field of Classification Search
CPC .................................... A61L 2/18; A61L 2/24
See application file for complete search history.

(56) References Cited

U.S. PATENT DOCUMENTS

| | | | | |
|---|---|---|---|---|
| 2,118,951 A | * | 5/1938 | Stienen | D06B 5/00 68/187 |
| 2,932,317 A | * | 4/1960 | Klosse | B01J 4/008 137/564.5 |
| 3,186,555 A | * | 6/1965 | Ventura | B65F 1/141 211/85.19 |
| 3,888,211 A | * | 6/1975 | Allen | A01K 39/0125 119/457 |
| 4,527,843 A | | 7/1985 | Murdoch | |
| 5,096,122 A | * | 3/1992 | Abramoska | B08B 9/0495 239/251 |
| 5,399,007 A | * | 3/1995 | Marconet | A61G 15/14 312/209 |
| 5,479,943 A | | 1/1996 | Kuhnell, III | |
| 5,498,394 A | | 3/1996 | Matschke | |
| 6,068,815 A | * | 5/2000 | Oberleitner | A01N 37/16 134/170 |
| 6,554,208 B1 | * | 4/2003 | Venuto, Sr. | A45D 44/00 239/207 |
| 6,558,620 B1 | * | 5/2003 | Sanford | A61B 1/123 134/102.2 |
| 6,582,654 B1 | | 6/2003 | Kral et al. | |
| 6,585,943 B1 | | 7/2003 | Sanford et al. | |
| 6,711,961 B2 | * | 3/2004 | Theriault | G01R 31/2849 73/865.6 |

(Continued)

FOREIGN PATENT DOCUMENTS

| | | |
|---|---|---|
| CN | 202635876 | 1/2013 |
| WO | 2007094553 | 8/2007 |
| WO | 2009086053 | 7/2009 |

*Primary Examiner* — Regina M Yoo
(74) *Attorney, Agent, or Firm* — Mercedes V. O'Connor; Rockman Videbeck & O'Connor

(57) ABSTRACT

A disinfecting apparatus for cleaning, disinfecting, and sanitizing restraining devices used by law enforcement and correctional facilities is designed to allow the disinfectant solution to evaporate that comprises a compartment that includes an interior chamber and a door, a disinfectant chamber for retaining the disinfectant solution, a plurality of jets, at least one plenum, an air compressor for conveying the disinfectant solution from the disinfectant chamber to the compartment through the plurality of jets, a power switch, and an electrical power plug to electrically connect the disinfecting apparatus to a power supply. The rear wall of the compartment includes a plurality of support structures to support a plurality of restraining devices within the interior chamber. The outer side of the rear wall of the compartment includes a mounting system that secures the disinfecting apparatus to a vertical, planar surface.

16 Claims, 1 Drawing Sheet

(56) References Cited

U.S. PATENT DOCUMENTS

| | | |
|---|---|---|
| 6,884,392 B2 | 4/2005 | Malkin et al. |
| 7,138,087 B1 | 11/2006 | Malkin et al. |
| 7,886,753 B2 | 2/2011 | Jonsson |
| D688,839 S | 8/2013 | Helm et al. |
| 8,815,174 B2 | 8/2014 | Bacik et al. |
| 2004/0091389 A1 | 5/2004 | Malkin et al. |
| 2004/0197248 A1 | 10/2004 | Hasegawa et al. |
| 2004/0232257 A1* | 11/2004 | Venuto, Sr. ............ A45D 44/00 239/200 |
| 2005/0121057 A1* | 6/2005 | Knowlton ................ A61L 2/18 134/68 |
| 2008/0099008 A1* | 5/2008 | Bolton .................... A21B 1/245 126/21 A |
| 2011/0110820 A1 | 5/2011 | Mann |
| 2015/0118107 A1* | 4/2015 | Sunkara ................... A61L 2/24 422/24 |

\* cited by examiner

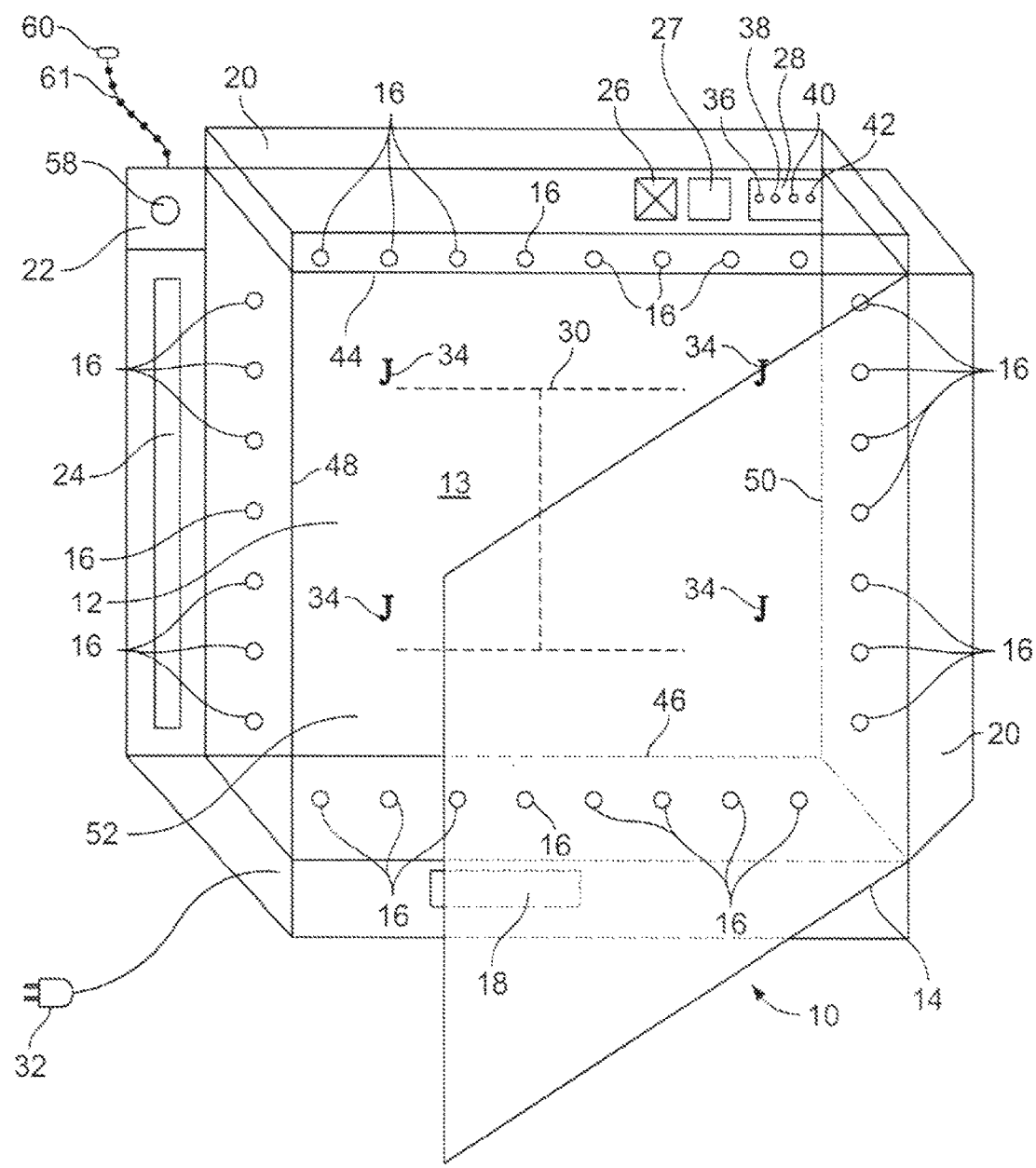

DISINFECTING APPARATUS FOR RESTRAINING DEVICES

BACKGROUND OF THE INVENTION

Field of the Invention

The present invention relates to a disinfecting apparatus for restraining devices, and more particularly, to a disinfecting apparatus that cleans, disinfects, and sanitizes restraining devices used by law enforcement and correctional facilities and that is designed to allow the disinfectant solution to substantially evaporate, eliminating the need for plumbing.

Description of the Prior Art

Law enforcement and correctional facilities utilize a wide variety of restraining devices such as handcuffs, shackles, and chains, to restrain individuals in their custody. The handcuffs, shackles, and chains make contact with the skin of the individual being restrained and with the skin of the law enforcement personnel applying the handcuffs, shackles, and chains. Over time, the restraining devices become dirty and can become contaminated with bacteria and disease. The restraining devices must be routinely cleaned, disinfected, and sanitized in order to prevent contamination and the spread of bacteria and disease. The disinfecting apparatus of the present invention is designed to clean, disinfect, and sanitize a plurality of restraining devices in a sealed chamber using an evaporating disinfectant solution or substantially evaporating disinfectant solution, eliminating the need for plumbing, drainage, or a backflow prevention device. The disinfecting apparatus of the present invention may also utilize a standard disinfectant solution as well.

U.S. Pat. No. 6,582,654 discloses a fluid spray system for cleaning and sterilizing medical devices on a rack that includes a fluid delivery system for an automated processor and includes spray nozzles for spraying and washing microbial decontaminant and rinsing solutions over a lumened device, such as an endoscope. The fluid delivery system also includes connection ports for connecting with internal passages of the device. A removable rack specially configured for the particular device, positions the device within a chamber. The spray nozzles are located on rear and side walls and on a door of the chamber and the nozzles are adapted to spray the device from all directions. Sets of the spray nozzles are pulsed in sequence so that the spray jets do not cancel each other out. Leaking connectors connect the automated processor connection ports with inlet ports of the device and allow a portion of the cleaning, decontaminant, and rinsing solutions to leak from each inlet port. A computer control system controls cleaning, decontamination, rinsing, and drying stages of a cycle, which are all carried out within the chamber. The system disclosed in the '654 patent includes a collection tank that receives the sprayed washing/decontaminant solution as it drips off the items. The '654 patent does not disclose a disinfecting apparatus that uses a substantially evaporating disinfectant solution, thereby eliminating the need for plumbing, drainage, and a backflow prevention device. The '654 patent also does not disclose a disinfecting apparatus that includes at least one plenum that connects a plurality of jets and evens out the pressure between each jet.

U.S. Pat. No. 6,585,943 discloses a liquid cleaning and sterilization system that includes a fluid delivery system for an automated processor that delivers washing, microbial decontaminant, and rinse fluids to spray nozzles in a chamber for spraying the fluids over a lumened device, such as an endoscope. The fluid delivery system also delivers the fluids to connection ports that connect with internal passages of the device. Leaking connectors connect the automated processor connection ports with the inlet ports of the device and allow a portion of the washing, decontaminant, and rinsing solutions to leak from each inlet port. A computer control system controls cleaning, decontamination, rinsing, and drying stages of a cycle, which are all carried out within the chamber. A door locking and latching mechanism ensures that the door remains locked during the washing, decontamination, and rinse cycle to avoid accidental injury to an operator from strong chemicals used in the system. The system disclosed in the '943 patent includes a collection tank that receives the sprayed washing/decontaminant solution as it drips off the items. The '943 patent does not disclose a disinfecting apparatus that uses a substantially evaporating disinfectant solution, thereby eliminating the need for plumbing, drainage, and a backflow prevention device. The '943 patent also does not disclose a disinfecting apparatus that includes at least one plenum that connects a plurality of jets and evens out the pressure between each jet.

U.S. Pat. No. 6,884,392 discloses an apparatus and method for steam reprocessing flexible endoscopes. The reprocessing system deploys steam to disinfect and/or sterilize the endoscopes, and designs, components, and methods for reducing or balancing the reprocessing cycle time and the effects of thermal expansion and contraction on the endoscopes. In one embodiment, the apparatus includes an enclosure having a reprocessing bay for receiving the endoscope and a steam source in fluid communication with the reprocessing bay. A fluid sprayer is included for spraying steam onto the external surface of the endoscope. In another embodiment, the method includes placing the endoscope into a steam reprocessing bay of a reprocessing apparatus, applying steam to the exterior surface of the endoscope, flowing steam through the lumen of the endoscope, and controlling a dimensional change to the endoscope during the reprocessing method. The apparatus of patent '392 connects to a cold and hot water source that is used in the steam generator. The '392 patent does not disclose a disinfecting apparatus that uses a substantially evaporating disinfectant solution, thereby eliminating the need for plumbing, drainage, and a backflow prevention device. The '392 patent also does not disclose a disinfecting apparatus that includes at least one plenum that connects a plurality of jets and evens out the pressure between each jet.

U.S. Pat. No. 7,886,753 discloses a disinfection apparatus for disinfecting liquid cleaning of health care objects and the like. The disinfection equipment includes a washing system for supplying liquid to a chamber that is adapted to hold the objects during cleaning, a pump for pumping liquid in the washing system, and at least one collection space connected to the inlet of the pump for collecting liquid from the chamber to the pump. The collection space is defined by at least one partition that has an extent horizontally from the inlet of the pump and that screens the inlet of the pump from liquid descending into the chamber at least nearing the inlet of the pump. The apparatus of patent '753 includes a drain pump that is connected to a sump for discharging used liquid to a drain. The '753 patent does not disclose a disinfecting apparatus that uses a substantially evaporating disinfectant solution, thereby eliminating the need for plumbing, drainage, and a backflow prevention device. The '943 patent also does not disclose a disinfecting apparatus that includes at least one plenum that connects a plurality of jets and evens out the pressure between each jet.

The prior art to date does not disclose a disinfecting apparatus that is designed to use a substantially evaporating disinfectant solution, thereby eliminating the need for plumbing, drainage, and a backflow prevention device. None of the prior art can be combined in a way to suggest the necessary modifications to produce the disinfecting apparatus of the present invention. There is no teaching, suggestion, or motivation that would have enabled a person of ordinary skill in the art to modify any prior disinfecting apparatus in the manner embodied in the present invention.

It is a primary object of the present invention to provide a disinfecting apparatus for restraining devices that is designed to use an evaporating disinfectant solution, thereby eliminating the need for plumbing, drainage, and a backflow prevention device.

Another object of the present invention is to provide a disinfecting apparatus for restraining devices that includes at least one plenum that connects a plurality of jets and evens out the pressure applied to each jet.

Still another object of the present invention is to provide a disinfecting apparatus for restraining devices that is designed to use an evaporating disinfectant solution that does not leave any biohazard residue.

Still another object of the present invention is to provide a disinfecting apparatus for restraining devices that reduces or eliminates human contact with the disinfectant solution.

Still another object of the present invention is to provide a disinfecting apparatus for restraining devices that cleans, disinfects, and sanitizes restraining devices used by law enforcement and correctional facilities.

SUMMARY OF THE INVENTION

The disinfecting apparatus for restraining devices of the present invention is designed to clean, disinfect, and sanitize restraining devices used by law enforcement and correctional facilities. The disinfecting apparatus is particularly designed to allow the disinfectant solution to substantially evaporate, thereby eliminating the need for plumbing, drainage, or a backflow prevention device. The disinfecting apparatus comprises a compartment that includes an interior chamber and a door, a disinfectant chamber for retaining a disinfectant solution, a plurality of jets, at least one plenum, an air compressor for conveying the disinfectant solution from the disinfectant chamber to the compartment through the plurality of jets, a power switch, and an electrical power plug to electrically connect the disinfecting apparatus to a power supply. The compartment includes a top wall, a bottom wall, a left wall, a right wall, and a rear wall having a first side and a second side opposite the first side. The plurality of jets are disposed in at least one of the top wall, bottom wall, left wall, and right wall of the compartment. The plenum is located on at least one of the top wall, bottom wall, left wall, and right wall of the compartment, each plenum connecting the plurality of jets on that particular wall and evening out the pressure applied to each jet. The plurality of jets conveys the disinfectant solution in a pulsed spray or a continuous mist spray to the restraining devices within the interior chamber of the compartment.

BRIEF DESCRIPTION OF THE DRAWINGS

The present invention is further described with reference to the accompanying drawings in which:

FIG. 1 is a front perspective view of a first embodiment of a disinfecting apparatus for restraining devices of the present invention showing a transparent door.

DETAILED DESCRIPTION OF THE ILLUSTRATED EMBODIMENTS

Law enforcement and correctional facilities utilize a wide variety of restraining devices, such as handcuffs, shackles, and chains, to restrain individuals in their custody. Over time, and through contact with surfaces and the skin of the individual being restrained and the law enforcement personnel applying the restraining device, the restraining devices become dirty and can become contaminated with dirt, bacteria, and disease. The restraining devices must be routinely cleaned and disinfected in order to prevent contamination and the spread of bacteria and disease. The disinfecting apparatus for restraining devices of the present invention is adapted to allow law enforcement personnel and correctional facility personnel to clean, disinfect, and sanitize a plurality of restraining devices safely within a sealed compartment, reducing or eliminating atmospheric contamination and biohazard residue.

In a first embodiment, shown in FIG. 1, the disinfecting apparatus 10 of the present invention comprises a compartment 12 that defines an interior chamber 13 and includes a door 14, a plurality of jets 16, an air compressor 18, at least one plenum 20, a disinfectant chamber 22 in communication with compartment 12, and an electrical power plug 32. The air compressor 18 conveys a disinfectant solution from the disinfectant chamber 22 to compartment 12 through the plurality of jets 16. The compartment 12 includes a top wall 44 opposite a bottom wall 46, a left wall 48 opposite a right wall 50, and a rear wall 52 having a first side and a second side opposite the first side. The plurality of jets are disposed in at least one of the top wall 44, the bottom wall 46, the left wall 48, and the right wall 50 of compartment 12. The plenum 20 is located on at least one of the top wall 44, bottom wall 46, left wall 48, and right wall 50 of compartment 12. The plenum 20 connects to the plurality of jets 16 located on that particular wall of compartment 12 in which the plenum 20 is located and the plenum 20 is adapted to even out the pressure to each jet in the plurality of jets 16 on that particular wall. The plurality of jets 16 conveys the disinfectant solution in a pulsed spray or a continuous mist spray to the restraining devices within interior chamber 13 of compartment 12. The plurality of jets 16 can also include stainless steel tips.

The first side of rear wall 52 of compartment 12 includes a plurality of support structures 34, such as hooks, adapted to hold at least one restraining device (not shown) per support structure 34 within interior chamber 13 and allowing the disinfecting apparatus 10 to potentially clean a plurality of restraining devices at one time. The rear wall 52 further includes a mounting system 30, located on the second side of rear wall 52 opposite the first side that includes the plurality of support structures 34, the mounting system 30 securing the disinfecting apparatus 10 to a vertical, planar surface.

The top portion of compartment 12 includes a power switch 26, a start button 27, and a light indicator panel 28 disposed on plenum 20. The light indicator panel 28 includes at least one of a low liquid light indicator 36, an in-use light indicator 38, a ready light indicator 40, and a power light indicator 42. The low liquid light indicator 36 is illuminated when the disinfectant solution reaches a predetermined level within the disinfectant chamber 22. The in-use light indicator 38 is illuminated once the start button 27 is pressed and the disinfecting apparatus 10 is in a cycle of operation. The ready light indicator 40 is illuminated when the disinfecting apparatus 10 is ready to commence a cycle of operation. The power light indicator 42 is illuminated when the power switch 26 is in the ON position, the electrical power plug 32 is electrically connected to a power source, and the disinfecting apparatus 10 is receiving power from the power source.

Door 14 includes a sealing gasket (not shown) that forms an air tight seal between door 14 and compartment 12 when door 14 is closed and prevents the disinfectant solution from escaping from interior chamber 13 of compartment 12 into the atmosphere. Door 14 includes a sensor (not shown) that shuts off air compressor 18 to terminate the cycle of operation of disinfecting apparatus 10 when the sensor detects that door 14 is opened during the cycle of operation. In a second embodiment, door 14 includes a timer (not shown) that maintains door 14 closed and locked for a predetermined amount of time while the disinfecting apparatus 10 is in a cycle of operation. Once the cycle of operation completes and the timer expires, door 14 is unlocked and the user can open door 14. In a third embodiment, the disinfecting apparatus 10 includes an emergency kill switch (not shown) that allows a user to immediately shut off the disinfecting apparatus 10 in an emergency situation when the emergency kill switch is activated.

The disinfectant chamber 22 is adapted to retain a predetermined amount of disinfectant solution and includes a clear display 24 that indicates the amount of disinfectant solution remaining within the disinfectant chamber 22. The disinfectant chamber 22 includes an aperture 58 allowing access to the interior of the disinfectant chamber 22 and a removable cover 60 closing access to the interior of the disinfectant chamber 22 when removable cover 60 engages aperture 58. The removable cover 60 is connected to the disinfectant chamber 22 through a chain 61 or similar means. In one embodiment, cover 60 includes one of a plug having a sealing gasket and a screw cap. The disinfectant solution is poured into the disinfectant chamber 22 through aperture 58.

When the disinfecting apparatus 10 is in a cycle of operation, the disinfectant solution, under the force of air compressor 18, is conveyed from disinfectant chamber 22 to the plurality of jets 16 to provide a pulsed spray or a continuous spray mist of disinfectant solution to the restraining devices within interior chamber 13 of compartment 12 and suspended from the plurality of support structures 34. The disinfectant solution can be conveyed directly from the disinfectant chamber 22 to the plurality of jets 16 or can be conveyed from the disinfectant chamber 22, through plenum 20, and then to the plurality of jets 16. The disinfectant solution is only dispensed from disinfectant chamber 22 when door 14 is in the closed position and an air tight seal has formed between door 14 and compartment 12.

The disinfecting apparatus 10 is a plug and go apparatus that only requires the user to engage electrical power plug 32 with a power source for operation. To use disinfecting apparatus 10, the user places restraining devices upon support structures 34 within interior chamber 13 of compartment 12 and closes door 14, forming an air tight seal between compartment 12 and door 14. When power switch 26 is placed in the ON position and the start button 27 is pressed, the air compressor 18 forces the disinfectant solution from disinfectant chamber 22 to the plurality of jets 16. Plenum 20 connects the plurality of jets 16 and ensures that the disinfectant solution is evenly dispensed from each jet 16. The disinfectant solution is dispensed from jets 16 in a pulsed spray or in a continuous spray mist onto restraining devices. Air compressor 18 is shut down to terminate the cycle of operation of disinfecting apparatus 10 if the sensor (not shown) has detected that door 14 has been opened prior to termination of the cycle of operation of the disinfecting apparatus 10. In the first embodiment of the present invention, the disinfectant solution substantially evaporates over a predetermined amount of time and the user can then open door 14. In the second embodiment of the present invention, the timer (not shown) maintains door 14 closed and locked for a predetermined amount of time while the disinfecting apparatus 10 is in a cycle of operation. Once the timer expires, door 14 is unlocked and the user can then open door 14. The disinfecting apparatus 10 and air compressor 18 are also shut down to immediately terminate the cycle of operation of the disinfecting apparatus 10 if the emergency kill switch is activated in an emergency situation.

In a fourth embodiment, the air compressor 18 forces the disinfectant solution from disinfectant chamber 22 to the plurality of jets 16. The disinfectant solution is dispensed from jets 16 in a pulsed spray or in a continuous spray mist onto the restraining devices within compartment 12. The air compressor 18 subsequently forces high pressure compressed air through the plurality of jets 16 to assist in evaporating the disinfectant solution and drying the restraining devices within compartment 12. A removable tray (not shown) is included below bottom wall 46 of compartment 12 to collect any remaining disinfectant solution that has not yet evaporated.

The foregoing description of an illustrated embodiment of the invention has been presented for purposes of illustration and description, and is not intended to be exhaustive or to limit the invention to the precise form disclosed. The description was selected to best explain the principles of the invention and practical application of these principles to enable others skilled in the art to best utilize the invention in various embodiments and various modifications as are suited to the particular use contemplated. It is intended that the scope of the invention not be limited by the specification, but be defined by the claims set forth below.

What is claimed is:

1. A disinfecting apparatus for cleaning and disinfecting at least one restraining device, the disinfecting apparatus comprising:

a. a compartment that defines an interior chamber, said compartment having a top wall opposite a bottom wall, a left wall opposite a right wall, and a rear wall having a first side and a second side opposite said first side;

b. a door in moveable communication with said compartment, said door adapted to alternately open and close access to said interior chamber;

c. a disinfectant chamber in communication with said compartment, said disinfectant chamber adapted to retain a disinfectant solution;

d. a plurality of jets disposed in at least one of said top wall, bottom wall, left wall, and right wall, said plurality of jets adapted to convey said disinfectant solution to said interior chamber in one of a pulsed spray and a continuous spray;

e. at least one plenum enclosing an outer surface of at least one pressurized wall, the at least one plenum adapted to convey the disinfectant solution from the disinfectant chamber to each jet of the plurality of jets located on the at least one pressurized wall with an equal pressure to each jet, wherein the at least one pressurized wall comprises at least one of the top wall, bottom wall, left wall, and right wall;

f. an air compressor adapted to convey at least one of the disinfectant solution from said disinfectant chamber to said compartment and high pressure compressed air to said compartment;

g. a power switch in communication with said compartment, said power switch having an ON position and an OFF position; and h. an electrical power plug adapted to electrically connect to a power source.

2. The disinfecting apparatus of claim 1, further comprising:
   a. a plurality of support structures disposed on the first side of said rear wall, each said support structure adapted to support the at least one restraining device.

3. The disinfecting apparatus of claim 1, further comprising:
   a. a mounting system disposed on the second side of said rear wall, said mounting structure adapted to secure the disinfecting apparatus to a vertical, planar surface.

4. The disinfecting apparatus of claim 1, further comprising:
   a. a light indicator panel having at least one of a low liquid light indicator, an in-use light indicator, a ready light indicator, and a power light indicator, said light indicator panel disposed on one of said bottom wall and said plenum;
   b. said low liquid light indicator adapted to signal when the disinfectant solution is below a predetermined level within said disinfectant chamber;
   c. said in-use light indicator adapted to signal when said disinfecting apparatus is in a cycle of operation;
   d. said ready light indicator adapted to signal when said disinfecting apparatus is ready to commence a cycle of operation; and
   e. said power light indicator adapted to signal when said power switch is in the ON position and said disinfecting apparatus is receiving electrical power from said power source.

5. The disinfecting apparatus of claim 1, wherein the door includes a sealing gasket adapted to form an air tight seal between said door and said compartment when said door is closed.

6. The disinfecting apparatus of claim 1, further comprising:
   a. a sensor disposed on said door, said sensor adapted to detect when said door is open; and
   b. said disinfecting apparatus deactivating said air compressor and automatically shutting off said disinfecting apparatus when said sensor detects that said door is open.

7. The disinfecting apparatus of claim 1, further comprising:
   a. a timer disposed on said door, said timer adapted to maintain said door closed and locked for a predetermined amount of time and adapted to unlock said door when the predetermined amount of time has elapsed.

8. The disinfecting apparatus of claim 1, wherein the disinfectant chamber includes a clear display window adapted to indicate the amount of disinfectant solution remaining within said disinfectant chamber.

9. The disinfecting apparatus of claim 1, further comprising:
   a. a kill switch adapted to immediately shut off said disinfecting apparatus in an emergency situation.

10. The disinfecting apparatus of claim 1, further comprising:
    a. an aperture disposed in said disinfectant chamber and allowing access to said disinfectant chamber, said aperture adapted to receive said disinfectant solution; and
    b. a removable cover adapted to engage said aperture and close access to said disinfectant chamber.

11. The disinfecting apparatus of claim 10, wherein the removable cover includes one of a sealing plug and a screw cap.

12. The disinfecting apparatus of claim 10, wherein the removable cover includes a chain connected to an outer chamber surface of said disinfectant chamber.

13. The disinfecting apparatus of claim 1, wherein the plurality of jets include stainless steel tips.

14. The disinfecting apparatus of claim 1, further comprising a start button adapted to commence a cycle of operation.

15. The disinfecting apparatus of claim 1, wherein the plurality of jets are adapted to convey high pressure compressed air to said interior chamber.

16. The disinfecting apparatus of claim 1, further comprising a removable tray disposed below said bottom wall, said removable tray adapted to collect said disinfectant solution.

* * * * *